US012685496B2

(12) United States Patent
Nayak et al.

(10) Patent No.: US 12,685,496 B2
(45) Date of Patent: Jul. 21, 2026

(54) INTEGRATED STATIONARY AND ROTATING COMPUTED TOMOGRAPHY GANTRY STRUCTURE WITH A UNIFIED DRIVE

(71) Applicant: GE Precision Healthcare LLC, Waukesha, WI (US)

(72) Inventors: Vishwanath Nayak, Bangalore (IN); Dhaval Pravinbhai Dangashiya, Ahmedabad (IN); Ramachandra Gururaja Rao, Bangalore (IN)

(73) Assignee: GE Precision Healthcare LLC, Waukesha, WI (US)

( * ) Notice: Subject to any disclaimer, the term of this patent is extended or adjusted under 35 U.S.C. 154(b) by 156 days.

(21) Appl. No.: 18/732,067

(22) Filed: Jun. 3, 2024

(65) Prior Publication Data

US 2025/0366800 A1     Dec. 4, 2025

(51) Int. Cl.
*A61B 6/00*      (2024.01)
*A61B 6/03*      (2006.01)

(52) U.S. Cl.
CPC ............ *A61B 6/035* (2013.01); *A61B 6/4476* (2013.01)

(58) Field of Classification Search
None
See application file for complete search history.

(56) References Cited

U.S. PATENT DOCUMENTS

| | | | |
|---|---|---|---|
| 7,020,233 B1 * | 3/2006 | Tybinkowski ....... | A61B 6/4417 |
| | | | 250/363.04 |
| 7,217,038 B2 | 5/2007 | Katou et al. | |
| 2016/0058398 A1 | 3/2016 | Jensch | |

FOREIGN PATENT DOCUMENTS

DE        102013221726        4/2015

OTHER PUBLICATIONS

U.S. Appl. No. 18/330,566, filed Jun. 7, 2023, Vishwanath Nayak.

* cited by examiner

*Primary Examiner* — Hoon K Song
(74) *Attorney, Agent, or Firm* — Fletcher Yoder, P.C.

(57)        ABSTRACT

An integrated gantry structure of a computed tomography (CT) imaging system includes a rotating component configured to couple to imaging components. The rotating component includes a drive mechanism integrated on the rotating component configured to drive rotation of the rotating component and the imaging components in response to a driving force, wherein the drive mechanism includes drive teeth. The integrated gantry structure also includes a stationary component configured to support the rotating component. The integrated gantry structure further includes a bearing disposed between the rotating component and the stationary component, wherein the bearing couples the rotating component to the stationary component.

14 Claims, 16 Drawing Sheets

INTEGRATED STATIONARY AND ROTATING COMPUTED TOMOGRAPHY GANTRY STRUCTURE WITH A UNIFIED DRIVE

BACKGROUND

The subject matter disclosed herein relates to imaging systems and, more particularly, to an integrated stationary and rotating computed tomography gantry structure with a unified drive.

Non-invasive imaging technologies allow images of the internal structures or features of a patient to be obtained without performing an invasive procedure on the patient. In particular, such non-invasive imaging technologies rely on various physical principles, such as the differential transmission of X-rays through the target volume or the reflection of acoustic waves, to acquire data and to construct images or otherwise represent the observed internal features of the patient.

For example, in computed tomography (CT) and other X-ray based imaging technologies, X-ray radiation spans a subject of interest, such as a human patient, and a portion of the radiation impacts a detector where the image data is collected. In digital X-ray systems a photodetector produces signals representative of the amount or intensity of radiation impacting discrete pixel regions of a detector surface. The signals may then be processed to generate an image that may be displayed for review. In CT imaging systems, a detector array, including a series of detector elements, produces similar signals through various positions as a gantry is displaced around a patient.

A gantry of CT imaging system includes a rotating portion and a stationary portion. In particular, in CT imaging systems, the rotating portion of the gantry is conventionally used to spin the X-ray source (e.g., X-ray tube) and detector components around the imaging volume in which the patient is positioned during a scan. The X-ray tube, collimator, and detector form the critical image chain components of the CT imaging system. These subsystems or components mechanically assembled on a CT gantry base (i.e., the rotating portion) are positioned in an X-ray beam path for image formation. The CT gantry base includes a bearing that is separately coupled to a large and heavy platter shaped gear pulley system driven by a motor that causes rotation of the CT gantry base (and the image chain components). In particular, the bearing is coupled to the stationary component with a bolted joint. All of these components are separately coupled via numerous bolted assemblies and sub-assemblies requiring a great deal of time and effort.

SUMMARY

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In one embodiment, an integrated gantry structure of a computed tomography (CT) imaging system is provided. The integrated gantry structure includes a rotating component configured to couple to imaging components. The rotating component includes a drive mechanism integrated on the rotating component configured to drive rotation of the rotating component and the imaging components in response to a driving force, wherein the drive mechanism includes drive teeth. The integrated gantry structure also includes a stationary component configured to support the rotating component. The integrated gantry structure further includes a bearing disposed between the rotating component and the stationary component, wherein the bearing couples the rotating component to the stationary component.

In another embodiment, a computed tomography (CT) imaging system is provided. The CT imaging system includes an integrated gantry structure. The integrated gantry structure includes a rotating component configured to couple to imaging components. The rotating component includes a drive mechanism integrated on the rotating component configured to drive rotation of the rotating component and the imaging components in response to a driving force, wherein the drive mechanism includes drive teeth. The integrated gantry structure also includes a stationary component configured to support the rotating component, wherein the rotating component and the stationary component form an annular recess. The integrated gantry structure further includes a wire race bearing disposed within the annular recess.

In a further embodiment, a method for forming an integrated gantry structure of a computed tomography imaging system is provided. The method includes providing a rotating component configured to couple to imaging components. The rotating component includes a drive mechanism integrated on the rotating component configured to drive rotation of the rotating component and the imaging components in response to a driving force, wherein the drive mechanism includes drive teeth. The method also includes disposing an annular retainer sleeve about the rotating component. The method further includes providing a stationary component configured to support the rotating component. The method even further includes inserting a portion of the rotating component into the stationary component with a bearing disposed within an annular recess defined by the portion of the rotating component and the stationary component, wherein portion of the rotating component is inserted until the annular retainer sleeve abuts the stationary component adjacent the annular recess to keep the rotating component coupled to the stationary component via the bearing.

BRIEF DESCRIPTION OF THE DRAWINGS

These and other features, aspects, and advantages of the disclosed subject matter will become better understood when the following detailed description is read with reference to the accompanying drawings in which like characters represent like parts throughout the drawings, wherein.

DETAILED DESCRIPTION

Figure 1:
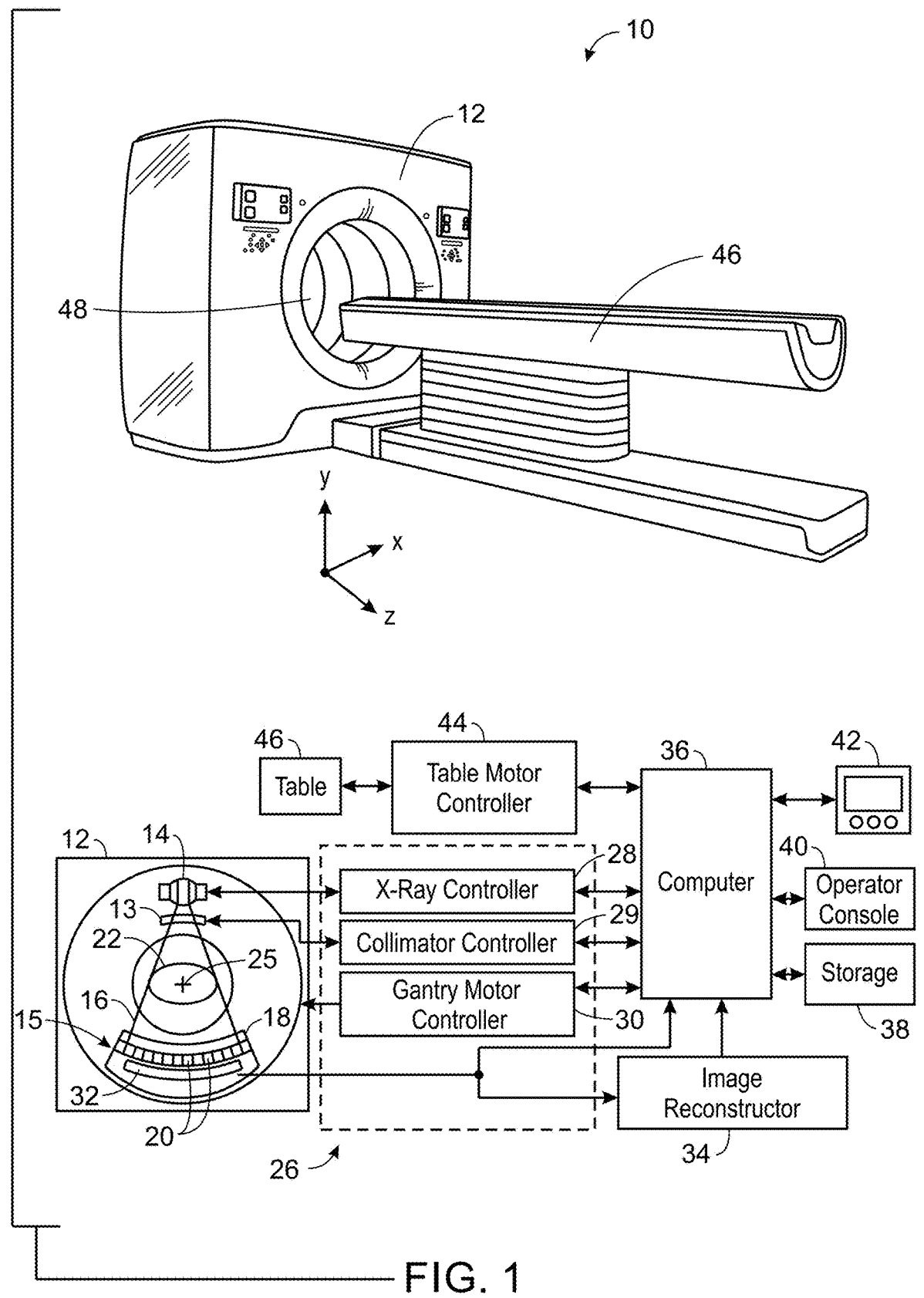
FIG. 1 is a combined pictorial view and block diagram of a computed tomography (CT) imaging system as discussed herein.
Figure 2:
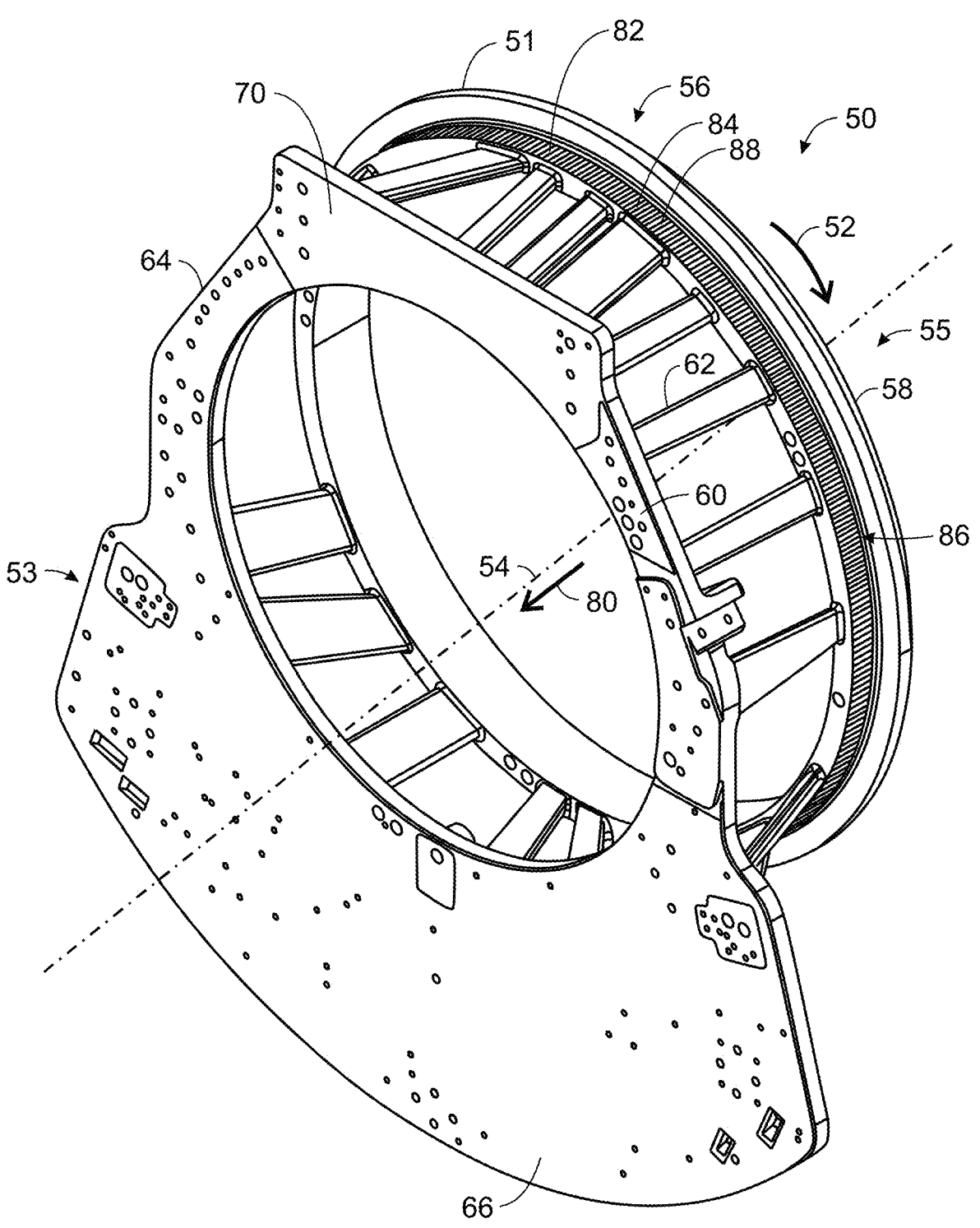
FIG. 2 is a perspective view of a CT rotating base and a sleeve, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While aspects of the following discussion are provided in the context of medical imaging, it should be appreciated that the disclosed techniques are not limited to such medical contexts. Indeed, the provision of examples and explanations in such a medical context is only to facilitate explanation by providing instances of real-world implementations and applications. However, the disclosed techniques may also be utilized in other contexts, such as image reconstruction for non-destructive inspection of manufactured parts or goods (i.e., quality control or quality review applications), and/or the non-invasive inspection of packages, boxes, luggage, and so forth (i.e., security or screening applications). In general, the disclosed techniques may be useful in any imaging or screening context or image processing or photography field where a set or type of acquired data undergoes a reconstruction process to generate an image or volume.

The present disclosure provides embodiments for an integrated stationary and rotating structure (e.g., rotating base or drum) for a CT gantry with a unified drive having multiple features such as an integrated bearing, an integrated drive mechanism, and mounting interfaces for various imaging components of the CT imaging system (e.g., X-ray source (e.g., X-ray tube), collimator, and X-ray detector assembly). All of these components are integrated into one component with a state-of-the-art machining process. The integrated stationary and rotating structure may be manufactured via machining, forging, moulding, casting, welding, or any three-dimensional (3D) printing process, or any combination of these processes. The architecture of the CT stationary frame enables the CT rotating base to be integrated either from the front side or the rear side of the CT stationary frame (i.e., retainer sleeve located on the front side or the rear side of the CT stationary frame).

The disclosed embodiments provide a rotating drum that is integrated directly (i.e., directly coupled) with the CT stationary frame via a wire race bearing, thus, eliminating the need for a separate externally mounted bearing. Unlike existing gantry structures having a rotating component with an endoskeleton structural architecture (i.e., rotating components are fitted inside the CT rotating base skeleton), the disclosed embodiments utilize an exoskeleton structural architecture (i.e., rotating components are projecting outside the CT rotating base skeleton) which results in a more compact footprint for the overall CT system. The disclosed embodiments also provide the rotating drum with an in-built drive mechanisms and provisions (e.g., unified drive) for any type of drive mechanism (e.g., v-groove/flat friction belt drive or timing belt drive with possibly gear teeth formed on the CT rotating base) that enable rotation of the imaging drum and the associated imaging components without any additional or intermittent requirement for separate drive provisions to transmit motion from the drive to the rotating portion of the gantry. A drive with gear teeth enables application of an external encoder with positive engagement to the drive, thus, eliminating feedback data loss due to slip which results in better rotational accuracy. The unified drive solution of the rotating drum makes the entire gantry structure plug and play fit, thus, eliminating any misalignments with the drive-driven system and enhancing motion performance. The integration of all of the components into a single integrated component eliminates the assembly alignment process of a drive wheel with respect to the rotating drum, eliminates the assembly alignment process of a rotating drum to a separate external bearing, and eliminates the assembly alignment process of a separate external bearing to a CT stationary frame.

The disclosed embodiments also provide improved image quality due to reduced gantry motion due to the integrated parts and elimination of tolerance stack up (e.g., due to fewer rotor deformations and better control of deformations in image chain components). Also, the elimination of tolerance stack up (due the integrated gantry structure) helps in alignment of X-ray tube and X-ray detector assembly and, thus, eliminates beam on window alignment requirement. The integrated gantry structure is also modular and scalable in design and may be utilized with other types of CT platforms. The integrated gantry structure further provides more structural robustness and rigidity, thus, making it scalable to higher rotation speed leading to helping in providing a faster scan time and a reduced X-ray dose provided to the patient.

The disclosed embodiments eliminate the use of Class-A bolted joints which results in a more robust and safer product. The disclosed embodiments also eliminate the run out alignment of a driven pulley with respect to a center of rotation, thus, reducing time and effort during assembly. The disclosed embodiments also do not require any special handling during both manufacturing and assembly since the rotating drum, bearing, stationary frame, and pulley are integrated into a single component. The disclosed embodiments also reduce assembly time and provide a lower part count (resulting in less inventory at manufacturing). The disclosed embodiments also lower the costs for CT systems in tier 3 cities in developing countries. The disclosed embodiments further reduce labor cost during manufacturing due to the simplification of the assembly process and reduction in parts to assemble. The integrated gantry structure provides a lightweight structure (e.g., having approximately 30 percent less overall gantry in comparison to existing CT gantry structures. The lightweight structure results in a reduction in transportation cost. The integrated gantry structure also provides a lower carbon footprint and compact form configured to fit into the least amount of space for installation due to a lesser Z-depth.

The disclosed embodiments provide an integrated gantry structure of a computed tomography (CT) imaging system that includes a rotating component configured to couple to imaging components. The rotating component includes a drive mechanism integrated on the rotating component configured to drive rotation of the rotating component and the imaging components in response to a driving force. The integrated gantry structure also includes a stationary component configured to support the rotating component. The integrated gantry structure further includes a bearing disposed between the rotating component and the stationary component, wherein the bearing couples the rotating component to the stationary component.

In certain embodiments, the rotating component is a single-piece structure. In certain embodiments, the single-piece structure includes features on the single-piece structure configured for mounting the imaging components on the single-piece structure. In certain embodiments, the imaging components comprise an X-ray source, a collimator, and an X-ray detector assembly. In certain embodiments, the integrated gantry structure includes a pulley or belt coupled to a motor disposed between the rotating component and the stationary component, wherein the pulley or belt coupled to the motor is configured to provide the driving force.

In certain embodiments, the rotating component and the stationary component form an annular recess, and the bearing is disposed within the annular recess. In certain embodiments, the annular recess is located within a width of the integrated gantry structure that extends in a direction along a rotational axis of the rotating component, wherein the width extends from a first outer surface of the rotating component facing away from the stationary component to a second outer surface of the stationary component facing away the rotating component. In certain embodiments, the rotating component includes a first annular structure having an outer surface facing away from a rotational axis of the rotating component in a radial direction perpendicular to the rotational axis, and the stationary component comprises a second annular structure having an inner surface facing toward the rotational axis in the radial direction, and wherein the annular recess is formed between an interface between the outer surface and the inner surface. In certain embodiments, the drive mechanism is located on the outer surface of the first annular structure adjacent a portion of the outer surface that interfaces with the inner surface of the second annular structure that forms the annular recess. In certain embodiments, the integrated gantry structure includes an annular retainer sleeve disposed about the outer surface of the first annular structure while abutting a lateral surface of the second annular structure, wherein the annular retainer sleeve is configured to keep the rotating component coupled to the stationary component via the bearing. In certain embodiments, the annular retainer sleeve is disposed about the outer surface of the first annular structure between the drive mechanism and the portion of the outer surface that interfaces with the inner surface of the second annular structure that forms the annular recess. In certain embodiments, the portion of the outer surface that interfaces with the inner surface of the second annular structure that forms the annular recess is disposed between the drive mechanism and where the annular retainer sleeve is disposed about the outer surface of the first annular structure.

In certain embodiments, the bearing includes a wire race bearing. In certain embodiments, the wire race bearing includes races made of an elastomer configured to dampen noise during rotation of the rotating component, to keep a bearing preload within a desired range, and to form an electrical insulation between the rotating component and the stationary component.

The disclosed embodiments provide a method for forming an integrated gantry structure of a computed tomography imaging system. The method includes providing a rotating component configured to couple to imaging components. The rotating component includes a drive mechanism integrated on the rotating component configured to drive rotation of the rotating component and the imaging components in response to a driving force. The method also includes disposing an annular retainer sleeve about the rotating component. The method further includes providing a stationary component configured to support the rotating component. The method even further includes inserting a portion of the rotating component into the stationary component with a bearing disposed within an annular recess defined by the portion of the rotating component and the stationary component, wherein portion of the rotating component is inserted until the annular retainer sleeve abuts the stationary component adjacent the annular recess to keep the rotating component coupled to the stationary component via the bearing.

With the preceding in mind and referring to FIG. 1, a computed tomography (CT) imaging system 10 is shown, by way of example. The CT imaging system 10 includes a gantry 12. The gantry 12 has an X-ray source 14 that projects a beam of X-rays 16 toward a detector assembly 15 on the opposite side of the gantry 12. The X-ray source 14 projects the beam of X-rays 16 through a pre-patient collimator assembly 13 that determines the size and shape of the beam of X-rays 16. The detector assembly 15 includes a collimator assembly 18 (a post-patient collimator assembly), a plurality of detector modules 20 (e.g., detector elements or sensors), and data acquisition systems (DAS) 32. The plurality of detector modules 20 detect the projected X-rays that pass through a subject or object 22 being imaged, and DAS 32 converts the data into digital signals for subsequent processing. Each detector module 20 in a conventional system produces an analog electrical signal that represents the intensity of an incident X-ray beam and hence the attenuated beam as it passes through the subject or object 22. During a scan to acquire X-ray projection data, gantry 12 and the components mounted thereon rotate about a center of rotation 25 (e.g., isocenter) so as to collect attenuation data from a plurality of view angles relative to the imaged volume.

Rotation of gantry 12 and the operation of X-ray source 14 are governed by a control system 26 of CT imaging system 10. Control system 26 includes an X-ray controller 28 that provides power and timing signals to an X-ray source 14, a collimator controller 29 that controls a length and a width of an aperture of the pre-patient collimator 13 (and, thus, the size and shape of the beam of X-rays 16), and a gantry motor controller 30 that controls the rotational speed and position of gantry 12. An image reconstructor 34 receives sampled and digitized X-ray data from DAS 32 and performs high-speed image reconstruction. The reconstructed image is applied as an input to a computer 36, which stores the image in a storage device 38. Computer 36 also receives commands and scanning parameters from an operator via console 40. An associated display 42 allows the operator to observe the reconstructed image and other data from computer 36. The operator supplied commands and parameters are used by computer 36 to provide control signals and information to DAS 32, X-ray controller 28, collimator controller 29, and gantry motor controller 30. In addition, computer 36 operates a table motor controller 44, which controls a motorized table 46 to position subject 22 and gantry 12. Particularly, table 46 moves portions of subject 22 through a gantry opening or bore 48.

FIGS. 2-5 illustrate different views of a CT rotating base 50 (e.g., drum) and a sleeve 51 (e.g., annular retainer sleeve). The CT rotating base 50 is a rotating component of a gantry (e.g., gantry 12 in FIG. 1) that is configured to be disposed within a housing of the gantry. The CT rotating base 50 is configured to be coupled to a stationary component via a bearing within the housing of the gantry. The CT rotating base 50 is configured to rotate in a circumferential direction 52 about an axis of rotation 54. The CT rotating base 50 includes a front portion 53 and a rear portion 55.

The CT rotating base 50 is made of a single-piece structure 56. The single-piece structure 56 may be manufactured via machining, forging, moulding, casting, weldment, or any three-dimensional (3D) printing process, or any combination of these processes. The single-piece structure 56 may made of aluminum, steel, or other metal, or metal alloy.

The single-piece structure 56 has a cylindrical shape. The single-piece structure 56 includes a first annular member or portion or structure 58 and a second annular member or portion or structure 60. The single-piece structure 56 also includes a plurality of structural members or cross bars 62 disposed between and coupled to both the first annular structure and the second annular structure. The plurality of cross bars 62 are spaced apart relative to each other in the circumferential direction 52 relative to the axis of rotation 54 of the single-piece structure 56 or the CT rotating base 50. The plurality of cross bars 62 are configured to provide the lowest amount of deflection and the lowest amount of stress. The CT rotating base 50 (i.e., the single-piece structure 56) is scalable in configuration and can be adapted for other CT platforms. A width 63 (e.g., shown in FIG. 5) of the plurality of cross bars 62 may vary. In particular, the width 63 of the plurality of cross bars 62 may be adjusted based on the configuration of the CT imaging system. Thus, a depth 65 (e.g., shown in FIG. 5) of the single-piece structure 56 in the direction 80 between the first annular structure 58 and the second annular structure 60 may also be adjusted based on the configuration of the CT imaging system. The depth 65 of single-piece structure minimizes the gantry depth. It should be noted that shape and/or arrangement of the CT rotating base 50 and/or the components of the CT rotating base 50 may vary from that depicted in FIGS. 2-5. For example, the location and angle of the cross bars 62 (e.g., relative to the axis of rotation 54 of the CT rotating base 50) may be different.

Returning to FIGS. 2-5, the second annular structure 60 includes an outer perimeter 64. The second annular structure 60 includes a first flat extension portion 66 (integral to the single-piece structure 56) that extends in a radial direction 68 (e.g., orthogonal to the axis of rotation 54) away from the axis of rotation 54 and the outer perimeter 64 of the second annular structure 60. The first flat extension portion 66 is configured for mounting (e.g., via openings or holes) of an X-ray detector assembly. The second annular structure 60 also includes a second flat extension portion 70 (integral to the single-piece structure 56) that extends in a radial direction 68 (e.g., orthogonal to the axis of rotation 54) away from the axis of rotation 54 and the outer perimeter 64 of the second annular structure 60. The second flat extension portion 70 is configured for mounting (e.g., via openings or holes) of both an X-ray source (e.g., X-ray tube) and a collimator.

Figure 3:
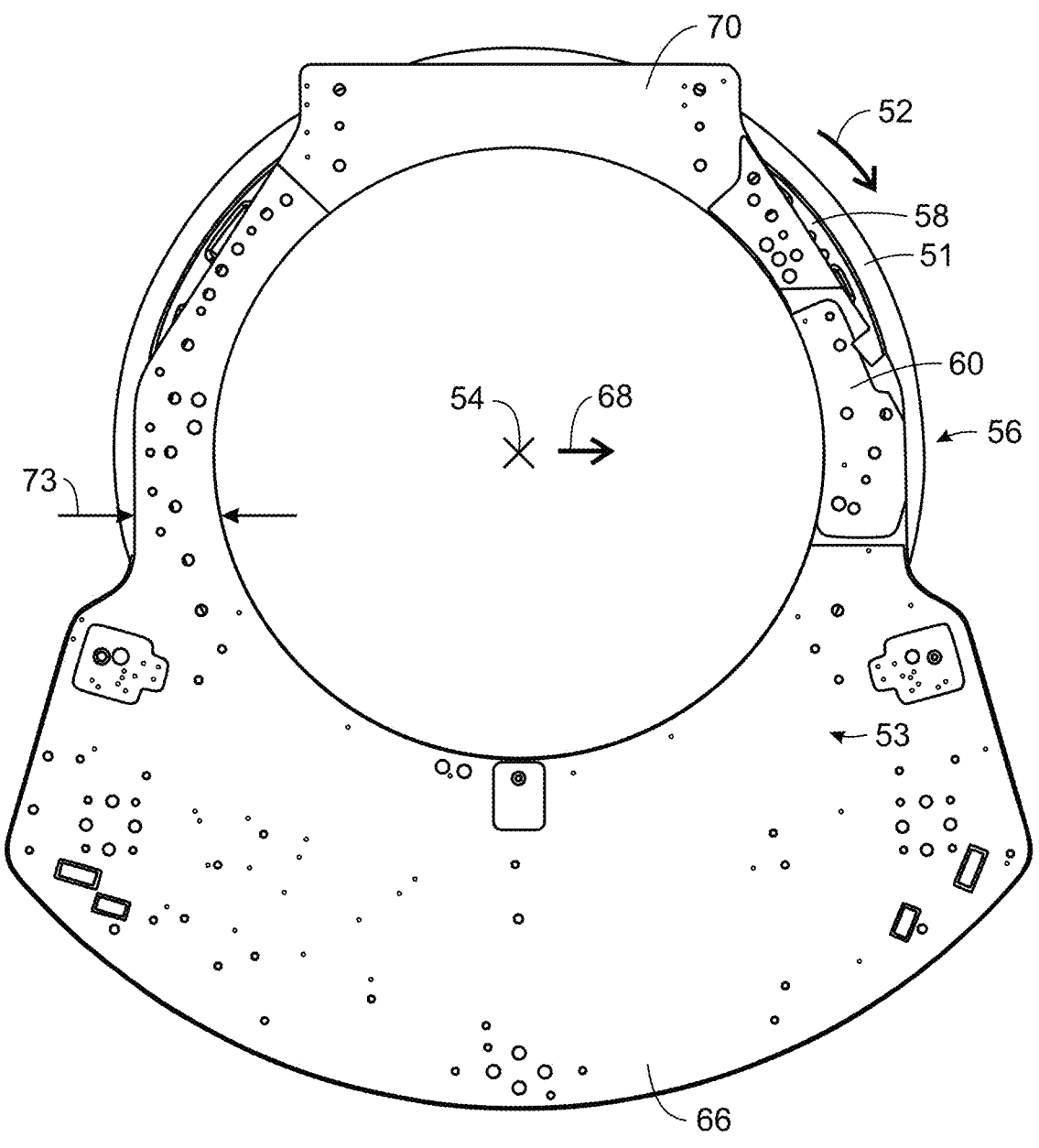
FIG. 3 is a front view of the CT rotating base and the sleeve in FIG. 2, in accordance with aspects of present disclosure.
Figure 4:
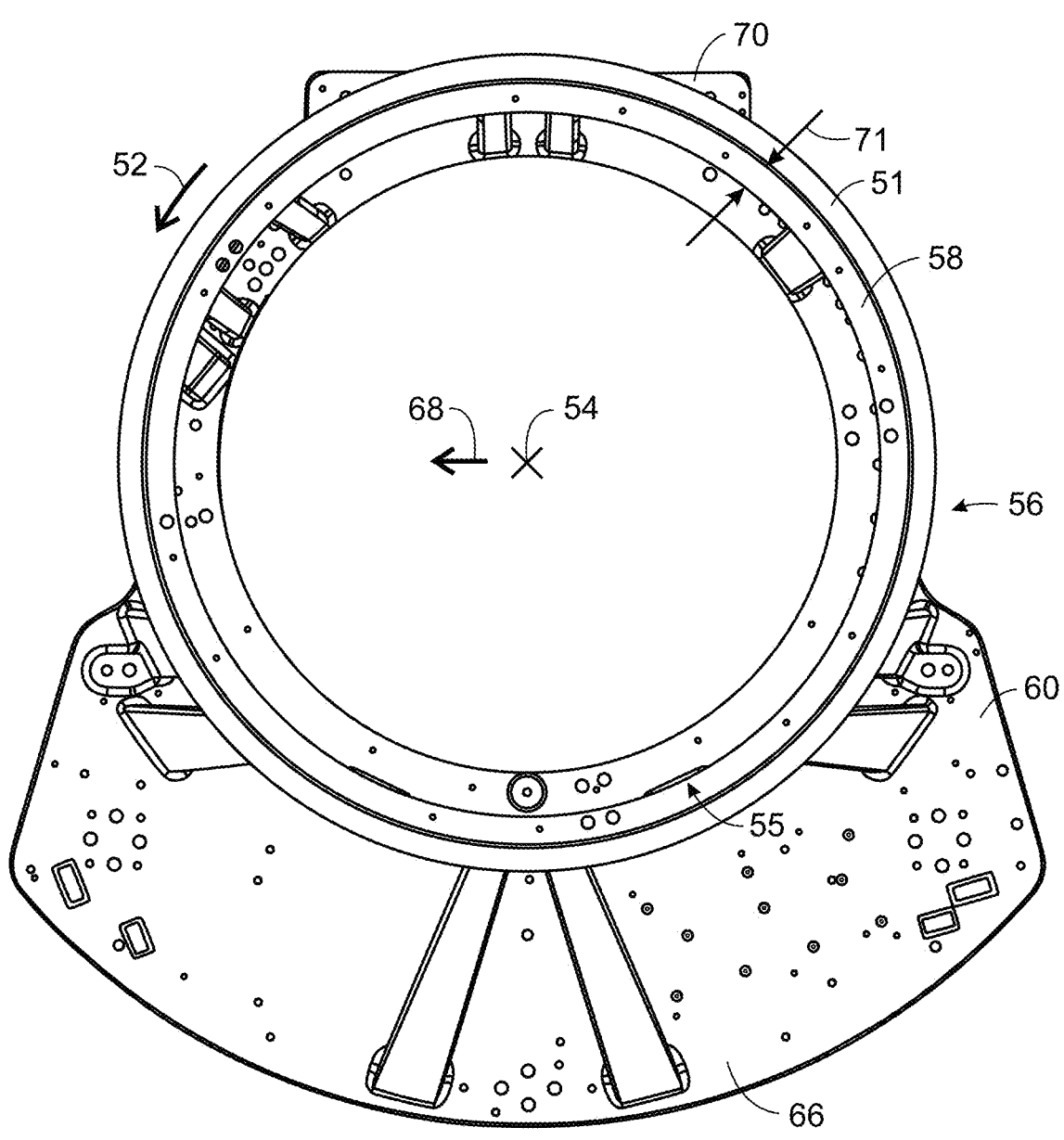
FIG. 4 is back view of the CT rotating base and the sleeve in FIG. 2, in accordance with aspects of the present disclosure.
Figure 5:
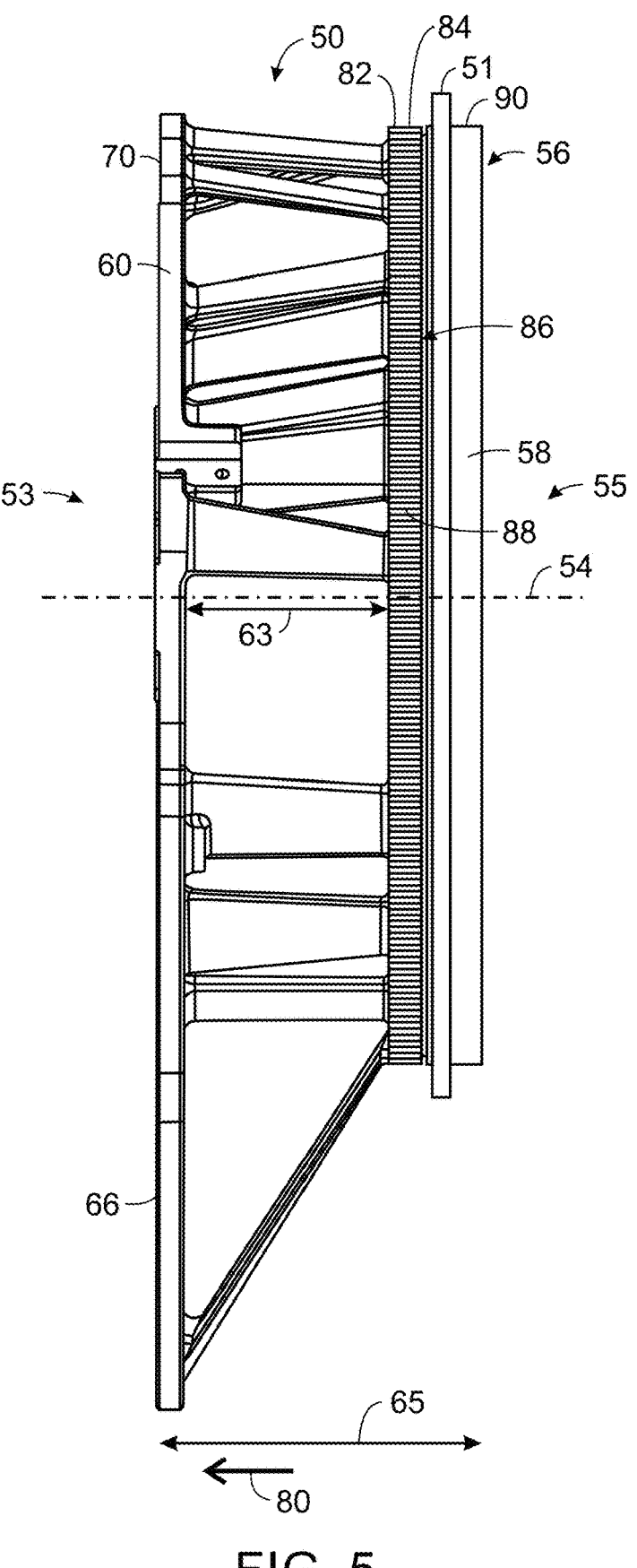
FIG. 5 is side view of the CT rotating base and the sleeve in FIG. 2, in accordance with aspects of the present disclosure.

As depicted in FIG. 4, a width 71 in the radial direction 68 of the first annular structure 58 may be constant in the circumferential direction 52. As depicted in FIG. 3, a width 73 in the radial direction 68 of the second annular structure 60 may vary in the circumferential direction 52. As depicted in FIGS. 3 and 4, the width 73 may be same, less, or greater than the width 71 at each corresponding point or location in the circumferential direction 52.

The single-piece structure 56 also includes a drive mechanism 82 integrated on the single-piece structure 56 that is configured to drive rotation of the single-piece structure 56 and the imaging components in response to a drive force (e.g., from a pulley or belt coupled to a motor). The drive mechanism 82 is located on a surface 84 (e.g., outer surface facing away from the axis of rotation 54) of an outer perimeter 86 of the first annular structure 58. As depicted, the surface 84 of the drive mechanism 82 includes teeth 88 (e.g., drive teeth or gear teeth). In certain embodiments, the drive mechanism 82 is flat or smooth. In certain embodiments, the drive mechanism 82 may include grooves. The built-in drive mechanism avoids needing any additional or intermittent separate driven provisions to transmit motion from the drive to the gantry that are typically required with rotating bases. In addition, the unified drive solution for the CT rotating base 50 provides an entire structure with a plug and play fit that eliminates any misalignments that occur with a drive-driven system while also enhancing motion performance and reliability of the drive system. Also, the integrated drive mechanism 82 eliminates the assembly alignment process of a drive wheel with a gantry rotating base. When the CT rotating base 50 is coupled to the CT stationary frame, the drive mechanism 82 is located between the CT rotating base 50 and the CT stationary frame.

The sleeve 51 is disposed about the outer surface 84 of the outer perimeter 86 of the first annular structure 58. In particular, the sleeve 51 is laterally disposed in the direction 80 between the drive mechanism 82 and a portion 90 of the first annular structure 58 that is inserted within the CT stationary frame. Although not shown in FIGS. 2-5, the outer surface 84 includes recesses that extend in the circumferential direction 52 about the outer surface 84 about the entire outer perimeter 86 that define (in conjunction with the CT stationary frame) a recess (e.g., annular recess) for a bearing (e.g., wire race bearing) that couples the CT rotating base 50 to the CT stationary frame. The sleeve 51 is configured to keep the CT rotating base 50 coupled to the CT stationary frame via the bearing. In particular, the sleeve 51 is configured to abut a lateral surface of an annular structure of the CT stationary frame when the portion 90 of the CT rotating base 50 is inserted into the CT stationary frame.

Figure 6:
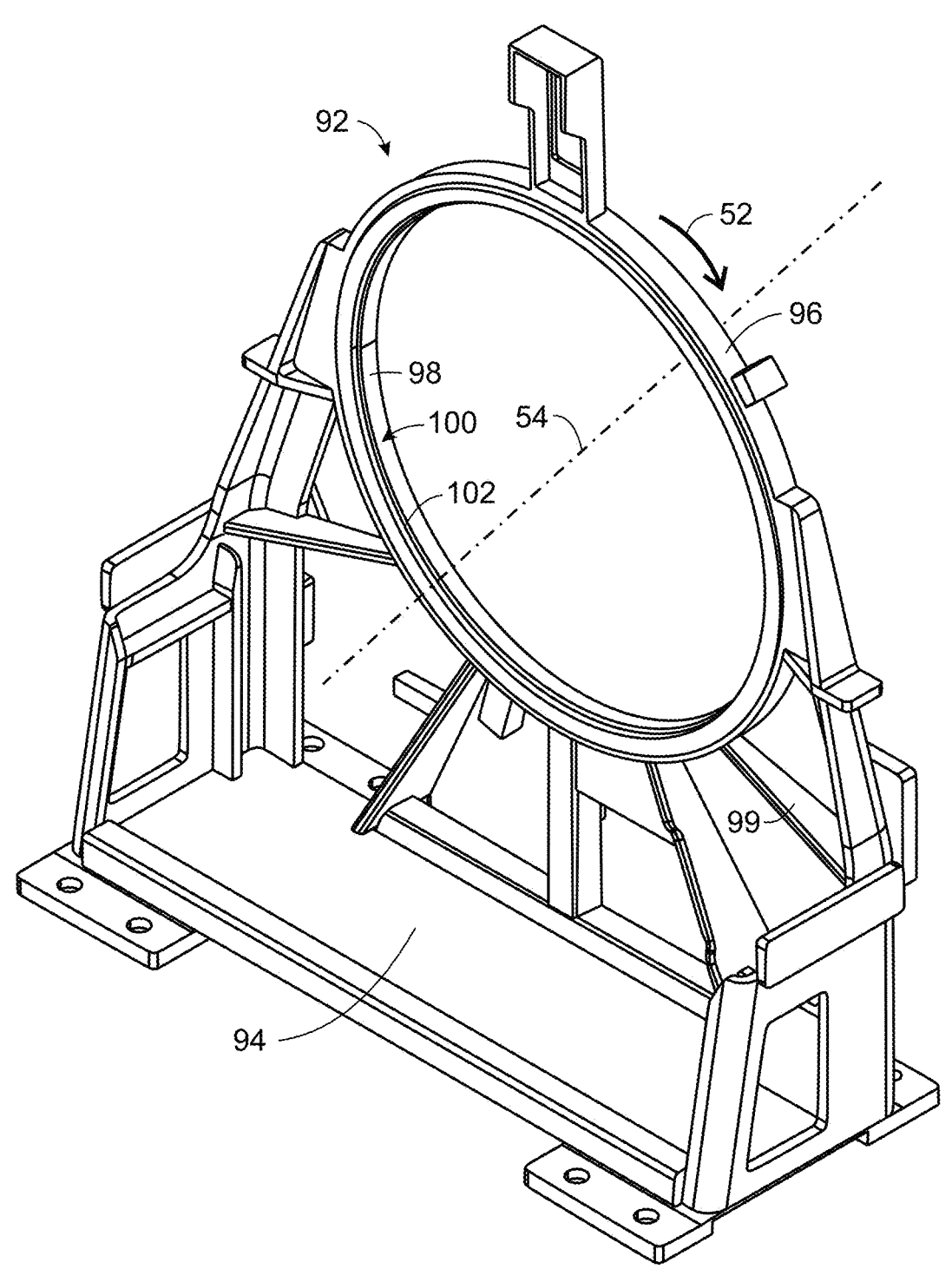
FIG. 6 is a perspective view of a CT stationary frame, in accordance with aspects of the present disclosure.

FIG. 6 is a perspective view of a CT stationary frame 92 (e.g., stationary component) that a rotating base (e.g., rotating base 50 in FIGS. 2-5)) is coupled to via an integrated bearing to form an integrated gantry structure. The CT stationary frame 92 includes a base 94 and an annular structure 96. Structural supports 99 extend between and couple the annular structure 96 to the base 94. A portion (e.g., portion 90 in FIG. 5) of the CT rotating base is inserted within the annular structure 96. An inner surface 98 of an inner perimeter 100 (e.g., facing towards the rotational axis 54) includes recesses that extend in the circumferential direction 52 about the inner surface 98 about the entire inner perimeter 100 that define (in conjunction with the CT rotating base) a recess (e.g., annular recess) for a bearing (e.g., wire race bearing) that couples the CT rotating base to the CT stationary frame 92. In addition, the annular structure 96 includes a lateral surface 102 (e.g., adjacent the inner surface 98 that defines the annular recess for the bearing) along the entire inner perimeter 100 that a sleeve (e.g., sleeve 51 in FIGS. 2-5) abuts against when the portion of the CT rotating base in inserted within the annular structure 96 of the CT stationary frame 92. The CT rotating base 50 is made of a single-piece structure 56. The CT stationary frame 92 may be manufactured via machining, forging, moulding, casting, weldment, or any three-dimensional (3D) printing process, or any combination of these processes. The CT stationary frame 92 may made of aluminum, steel, or other metal, or metal alloy. In certain embodiments, the CT stationary frame 92 may be a single-piece structure.

Figure 7:
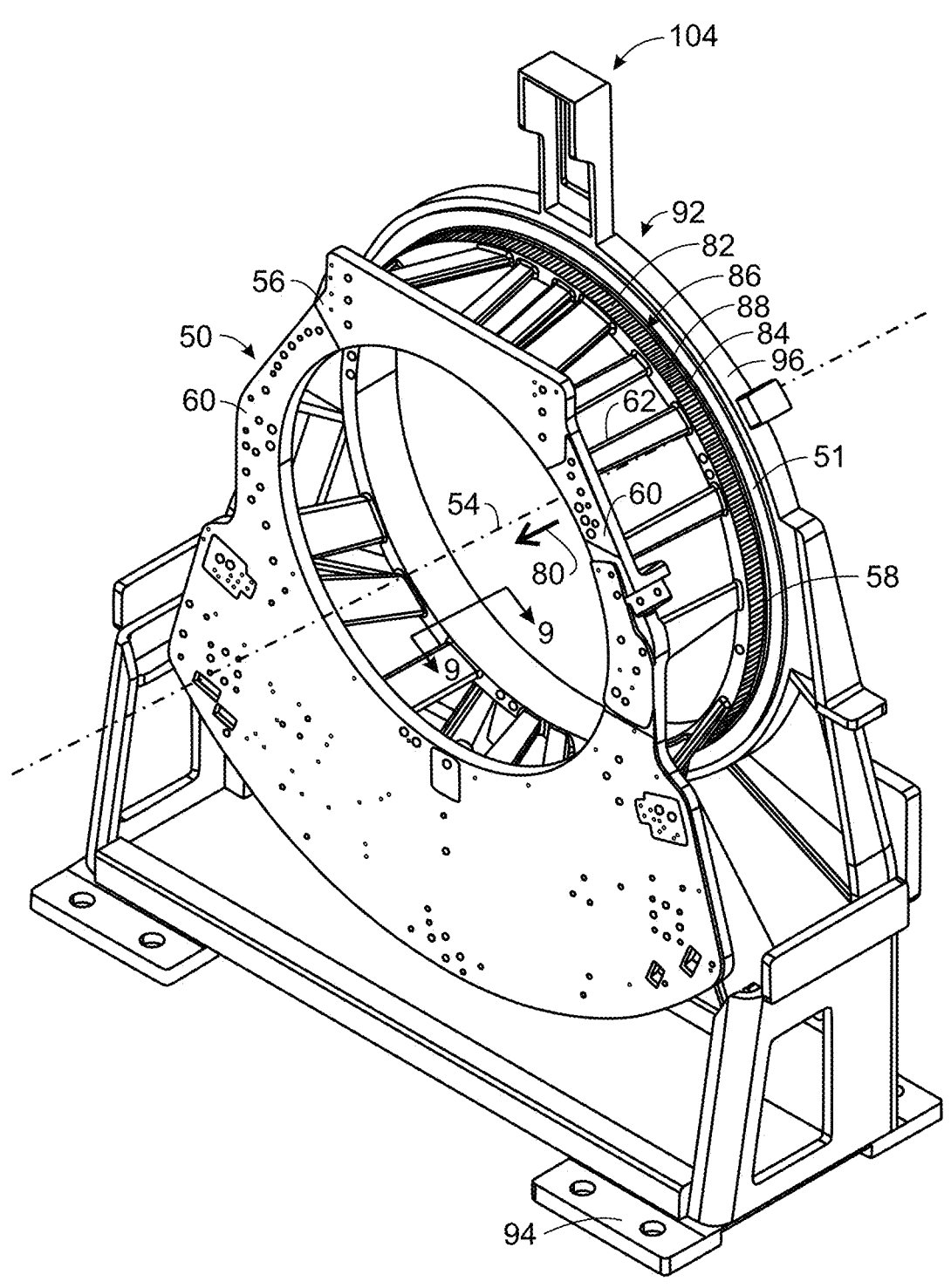
FIG. 7 is a perspective view of an integrated CT gantry structure, in accordance with aspects of the present disclosure.
Figure 8:
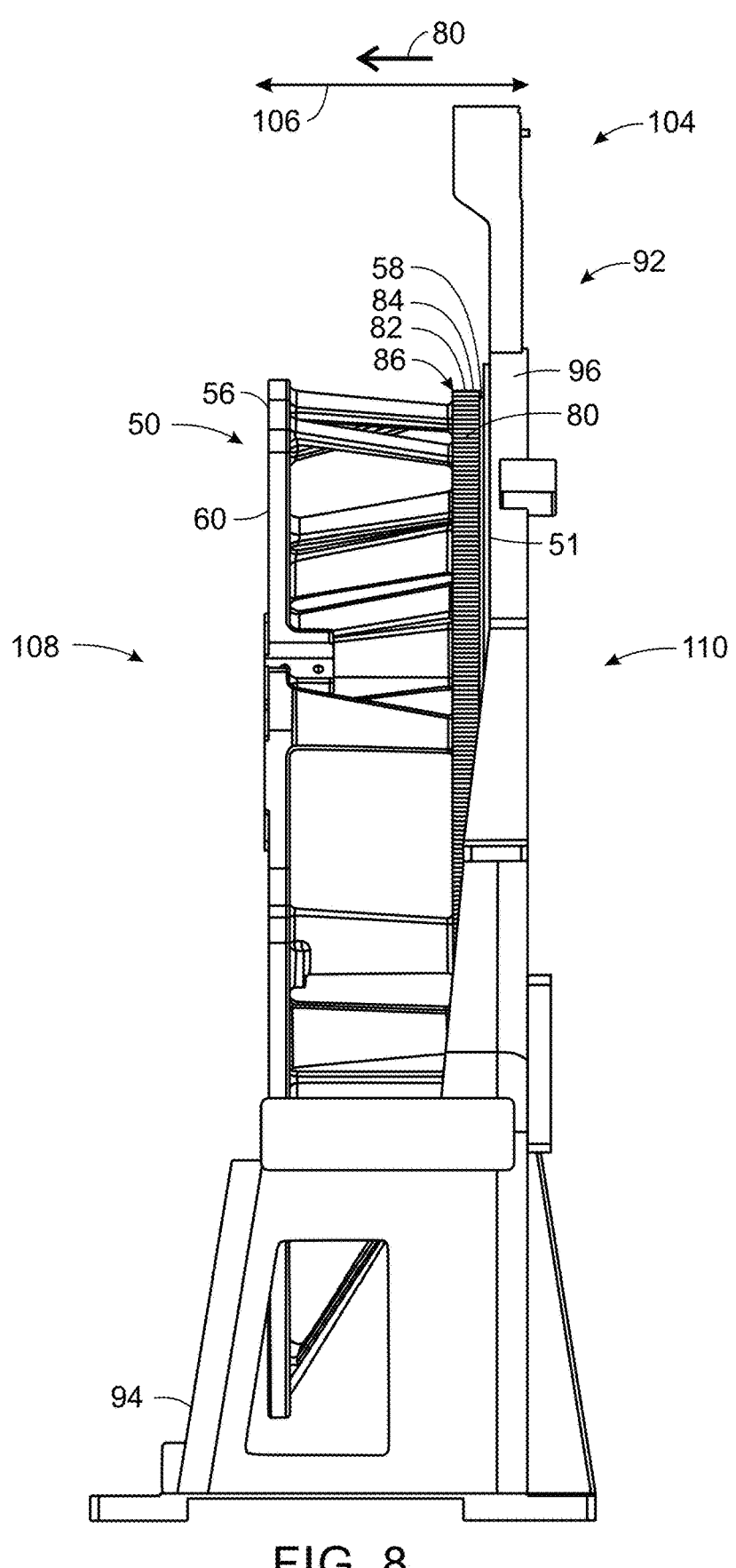
FIG. 8 is a side view of the CT integrated gantry structure in FIG. 7, in accordance with aspects of the present disclosure.

FIGS. 7 and 8 are different views of an integrated CT gantry structure 104. The integrated gantry structure 104 includes the CT rotating base 50 coupled to the CT stationary frame 92. In particular, a portion (e.g., portion 90 in FIG. 5) of the CT rotating base 50 inserted into the annular structure 96 of the CT stationary frame 92. The inserted portion of the CT rotating base 50 and an inner surface of the annular structure 96 define a recess to receive a bearing that couples the CT rotating base 50 and the annular structure 96. As depicted, the sleeve 51 abuts against a lateral surface (e.g., adjacent the inner surface that defines the annular recess for the bearing) along the entire inner perimeter of the annular structure 96 with the portion of the CT rotating base 50 inserted within the annular structure 96 of the CT stationary frame 92. In particular, the annular recess (and the bearing) are located within a width 106 of the integrated gantry structure 104 that extends in the direction 80 along the rotational axis 54 of the CT rotating base 50. The width 106 extends from a first outer surface 108 (on the second annular structure 60) of the CT rotating base 50 facing away from the CT stationary frame 92 to a second outer surface 110 of the CT stationary frame 92 (on the annular structure 96) facing away the CT rotating base 50.

As noted above, the CT rotating base 50 includes the drive mechanism 82 integrated on the single-piece structure 56 that is configured to drive rotation of the single-piece structure 56 and the imaging components in response to a drive force (e.g., from a pulley or belt coupled to a motor). The drive mechanism 82 is located on the surface 84 (e.g., outer surface facing away from the axis of rotation 54) of the outer perimeter 86 of the first annular structure 58. As depicted, the surface 84 of the drive mechanism 82 includes teeth 88 (e.g., drive teeth or gear teeth). In certain embodiments, the drive mechanism 82 is flat or smooth. In certain embodiments, the drive mechanism 82 may include grooves. The drive mechanism 82 is disposed within the integrated CT gantry structure 104 between the CT rotating base 50 and the CT stationary frame 92. In particular, the drive mechanism 82 is located within the width 106 of the integrated gantry structure 104. The integrated gantry structure 104 includes a pulley or belt coupled to a motor and disposed about the drive mechanism 82 that provides a drive force.

Figure 9:
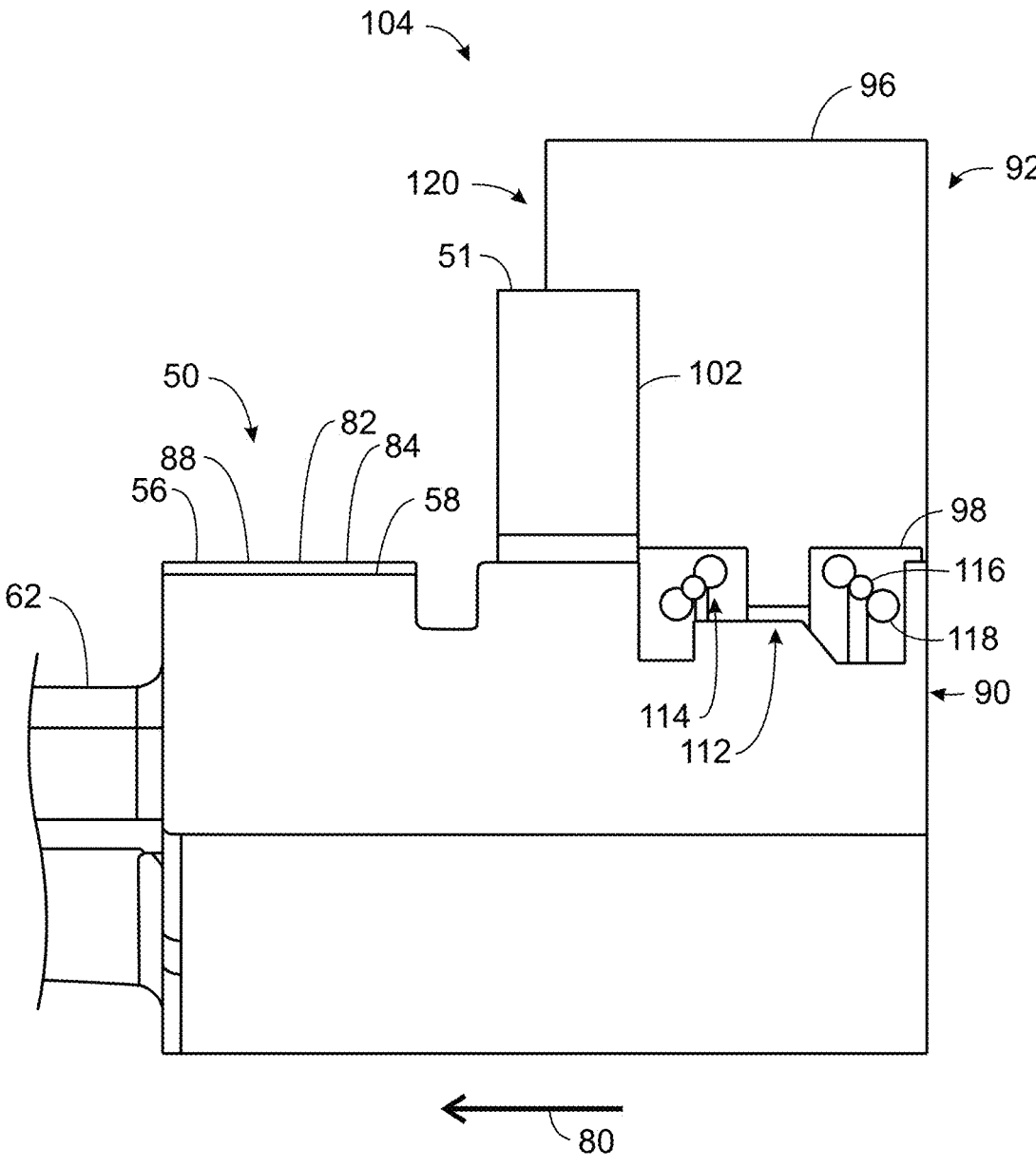
FIG. 9 is a side view of a cross-section of the CT integrated gantry structure in FIG. 7, taken along line 9-9, in accordance with aspects of the present disclosure.
Figure 10:
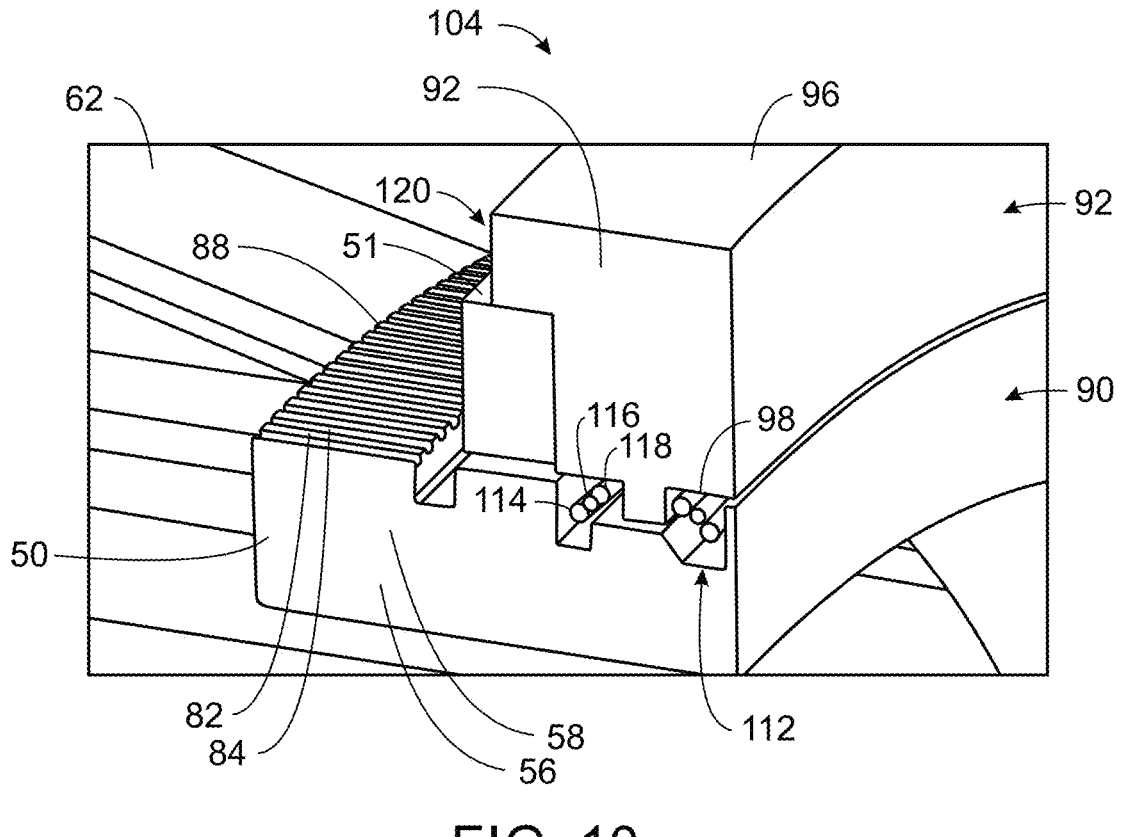
FIG. 10 is a perspective view of the cross-section in FIG. 9, in accordance with aspects of the present disclosure.

FIGS. 9 and 10 are different views of a cross-section of the integrated gantry structure 104 taken along line 9-9 in FIG. 7. As depicted, the portion 90 of the CT rotating base 50 (of the first annular structure 58) is inserted within the annular structure 96. The inner surface 98 of the annular structure 96 and the outer surface 84 of the first annular structure 58 (along the portion 90) together form or define a recess 112 (e.g., annular recess) for a bearing 114 (e.g., wire race bearing) that couples the CT rotating base 50 to the CT stationary frame 92. The bearing 114 extends 360 degrees in the circumferential direction relative to the rotational axis of the CT rotating base 50. The bearing 114 includes balls 116 disposed on races 118. The races 118 are made of an elastomer configured to dampen noise during rotation of the CT rotating base 50, to keep a bearing preload within a desired range, and to form an electrical insulation between the CT rotating base 50 and the CT stationary frame 92. As depicted, the sleeve 51 abuts against the lateral surface 102 (e.g., adjacent the inner surface 98 that defines the annular recess 112 for the bearing 114). The sleeve 51 is disposed in the direction 80 along the rotational axis of the CT rotating base between the drive mechanism 82 and the bearing 114 (and annular recess 112). As depicted, the sleeve 51 is disposed on a front side 120 of the annular structure 96 of the CT stationary frame 92.

Figure 11:
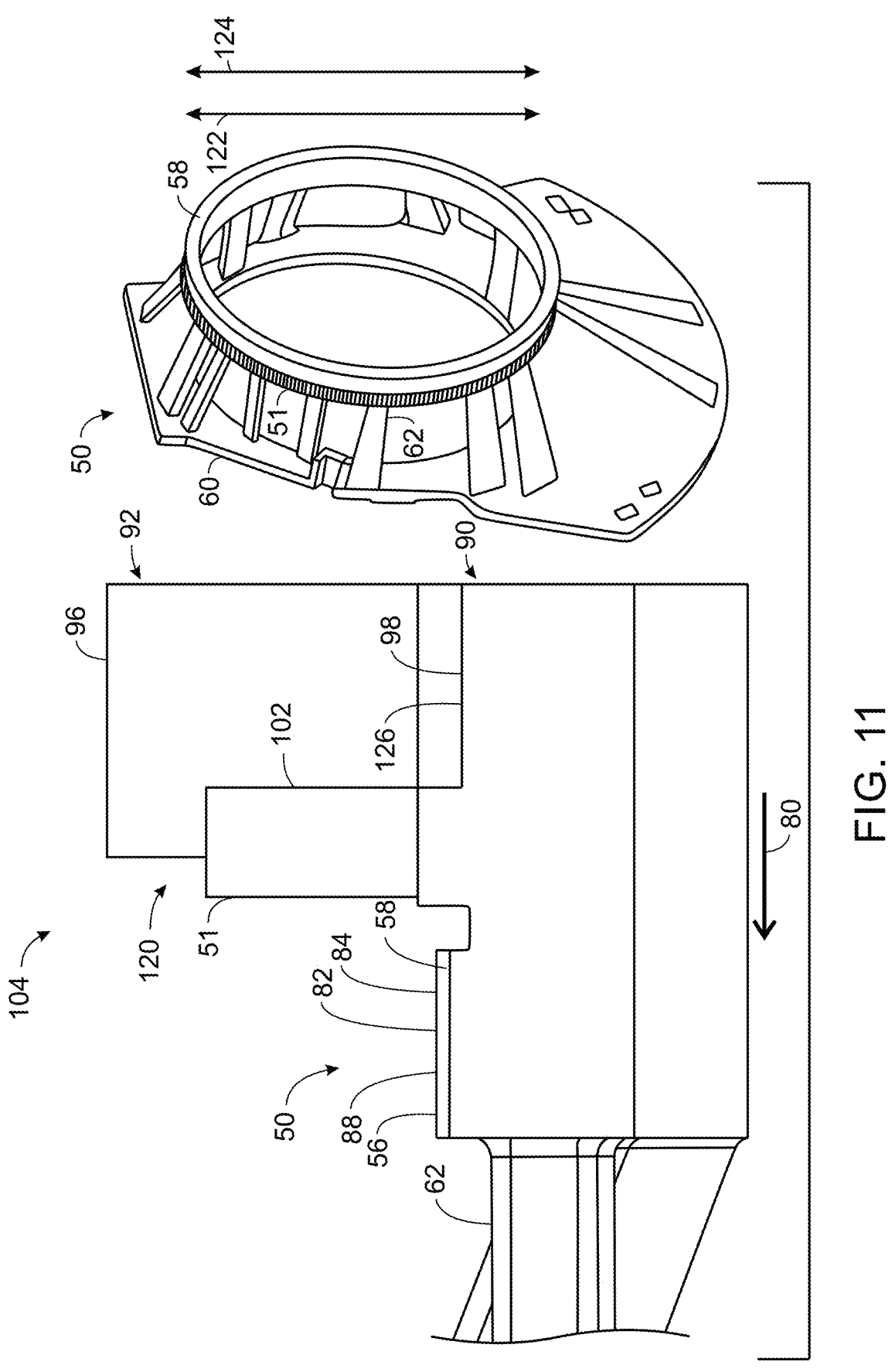
FIG. 11 is a side view of a cross-section of a CT integrated gantry structure and a perspective view of a CT rotating base of the CT integrated gantry structure, in accordance with aspects of the present disclosure.
Figure 12:
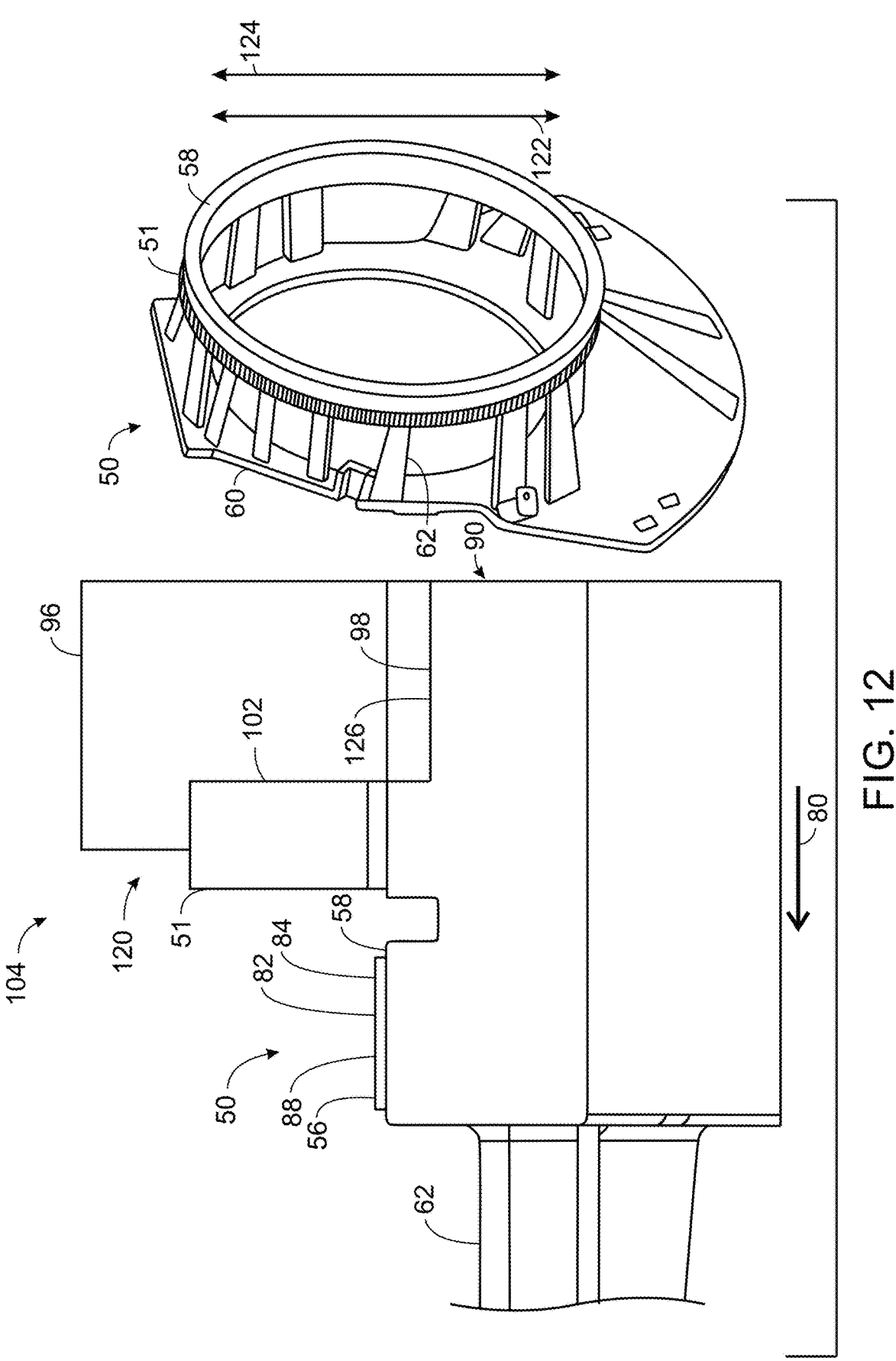
FIG. 12 is a side view of a cross-section of a CT integrated gantry structure and a perspective view of a CT rotating base of the CT integrated gantry structure, in accordance with aspects of the present disclosure.
Figure 13:
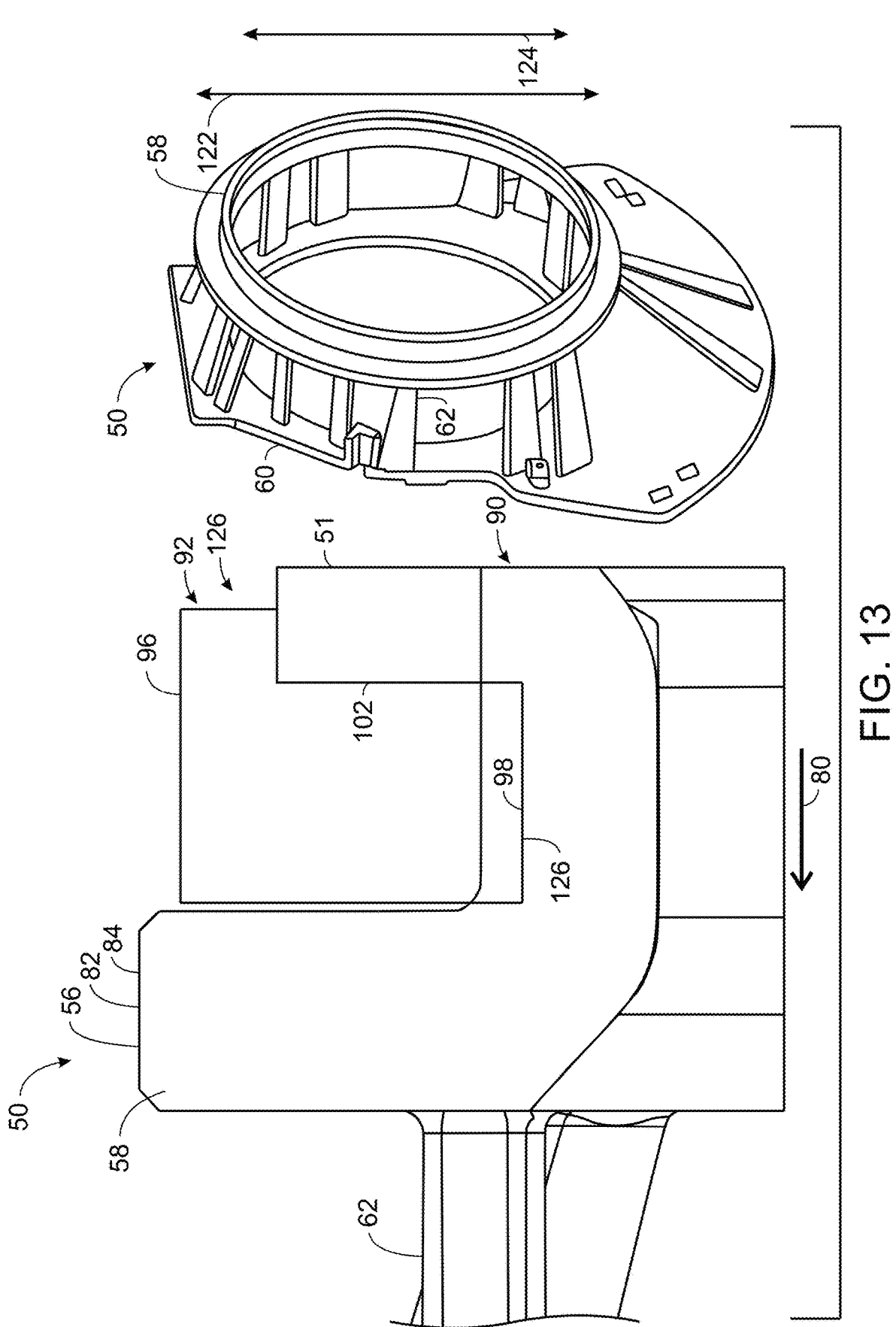
FIG. 13 is a side view of a cross-section of a CT integrated gantry structure and a perspective view of a rear of a CT rotating base of the CT integrated gantry structure, in accordance with aspects of the present disclosure.

Certain dimensions and configurations of the CT integrated gantry structure 104 may vary. For example, drum diameter, wire race diameter, driving belt length, and location of the retainer sleeve 51 may vary. FIGS. 11-13 each include a side view of a cross-section of the CT integrated gantry structure 104 (on left side) and a perspective view of a rear of the respective CT rotating base 50 of the CT integrated gantry structure 104 (on right side). The details of the bearing disposed in the annular recess are not shown in FIGS. 11-13. Each CT rotating base 50 in FIGS. 11-13 has a drum diameter 122. Each CT rotating base 50 in FIGS. 11-13 has a wire race diameter 124 (which is equivalent to the location of an interface 126 between outer surface 84 of the first annular structure 58 and the inner surface 98 of the annular structure 96). The driving belt length is determined by the outer diameter of the first annular structure 58 where the drive mechanism 82 is located.

The drum diameter 122 of the CT rotating base 50 in FIG. 11 is smaller than the drum diameters 122 of the CT rotating bases 50 in FIGS. 12 and 13. The drum diameter 122 of the CT rotating base 50 in FIG. 13 is larger than the drum diameters 122 of the CT rotating bases 50 in FIGS. 11 and 12. The wire race diameter 124 of the CT integrated gantry structure 104 of in FIG. 11 is smaller than the wire race diameter 124 of the CT integrated gantry structure 104 in FIG. 12. The wire race diameter 124 of the CT integrated gantry structure 104 in FIG. 13 is smaller than the wire race diameters 124 of the CT integrated gantry structures 104 in FIGS. 11 and 12. The driving belt length of the CT integrated gantry structure 104 of in FIG. 11 is smaller than the driving belt length of the CT integrated gantry structure 104 in FIG. 12. The driving belt length of the CT integrated gantry structure 104 in FIG. 13 is larger than the driving belt lengths of the CT integrated gantry structures 104 in FIGS. 11 and 12. As depicted in FIGS. 11 and 12, the CT integrated gantry structures 104 have the annular retainer sleeve 51 disposed on the front side 120 of the annular structure 96 of the CT stationary frame 92. As depicted in FIG. 13, the CT integrated gantry structure 104 has the annular retainer sleeve 51 disposed on a rear side 128 of the annular structure 96 of the CT stationary frame 92.

Figure 14:
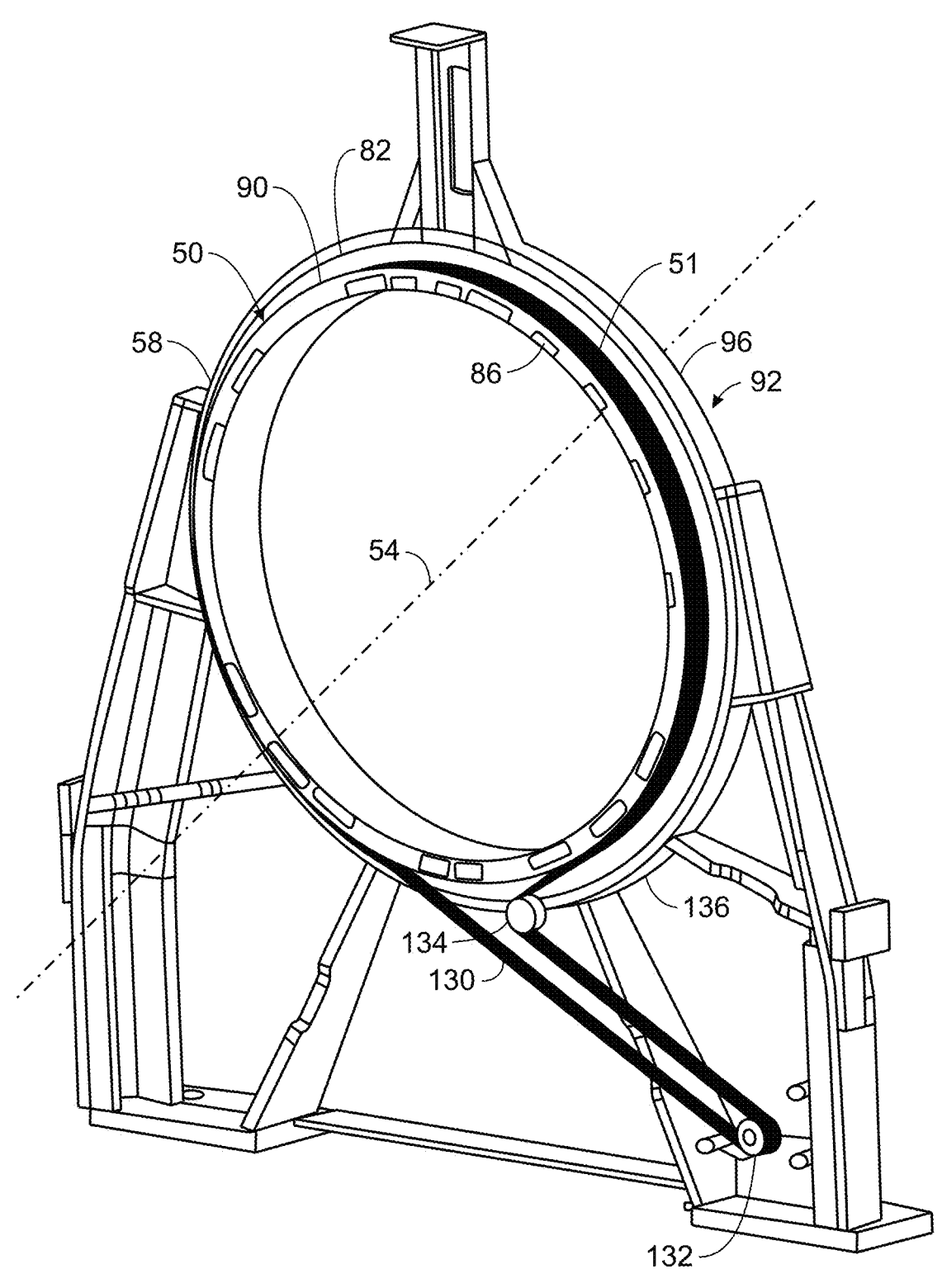
FIG. 14 is a perspective view of a pulley or belt coupled to a motor coupled to the CT integrated gantry structure in FIG. 7 (e.g., showing only a first annular structure of the CT rotating base inserted in the CT stationary frame), in accordance with aspects of the present.
Figure 15:
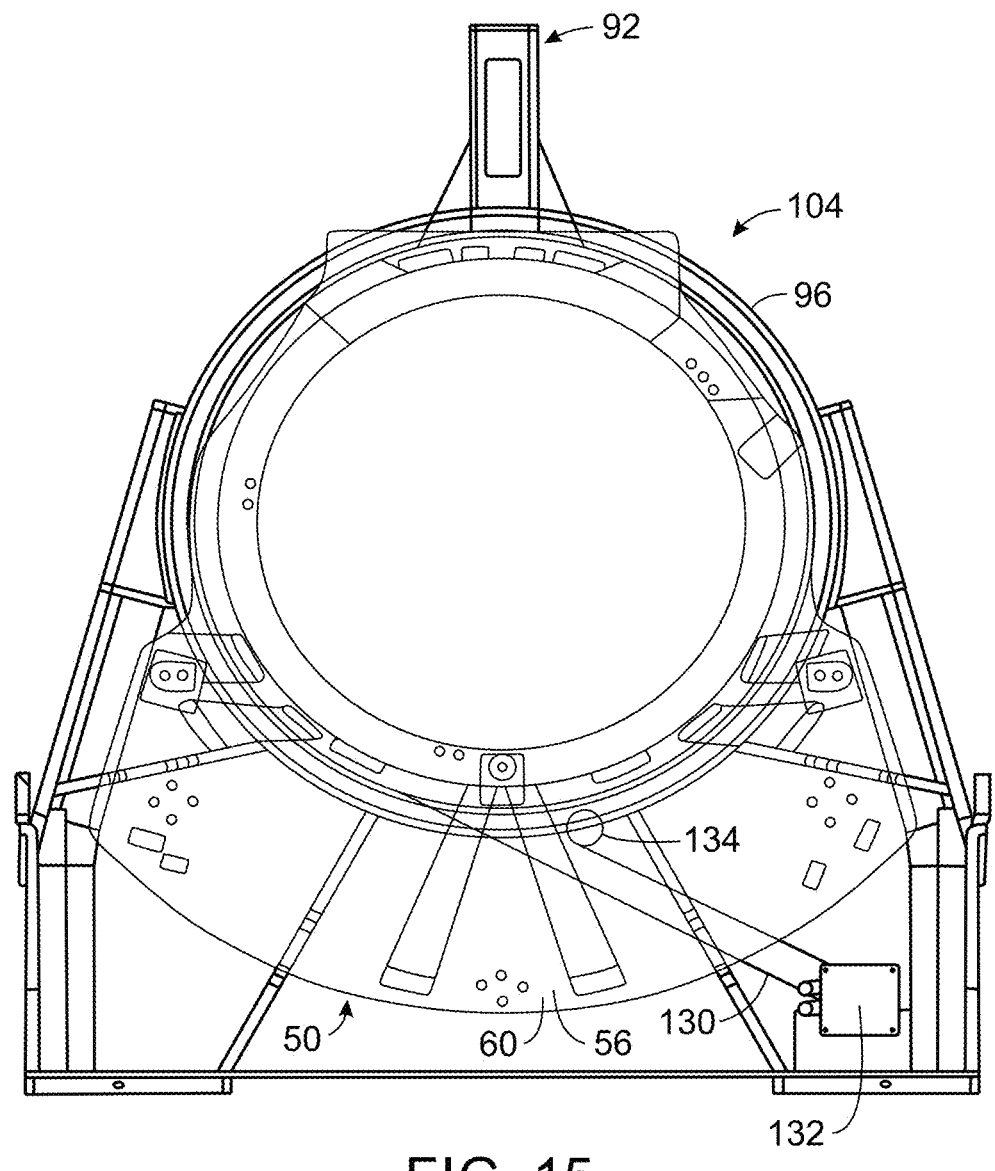
FIG. 15 is a front view of the pulley or belt coupled to the motor coupled to the CT integrated gantry structure in FIG. 7, in accordance with aspects of the present disclosure.

FIGS. 14 and 15 are different views of a pulley or belt 130 coupled to a motor 132 coupled to the CT integrated gantry structure 104 in FIG. 7. The CT integrated gantry structure 104 includes the CT rotating base 50 coupled to the CT stationary frame 92. In particular, the portion 90 of the CT rotating base 50 is inserted into the annular structure 96 of the CT stationary frame 92. The inserted portion 90 of the CT rotating base 50 and an inner surface of the annular structure 96 define a recess to receive a bearing that couples the CT rotating base 50 and the annular structure 96. As depicted, the sleeve 51 abuts against a lateral surface (e.g., adjacent the inner surface that defines the annular recess for the bearing) along the entire inner perimeter of the annular structure 96 with the portion of the CT rotating base 50 inserted within the annular structure 96 of the CT stationary frame 92.

As noted above, the CT rotating base 50 includes the drive mechanism 82 integrated on the single-piece structure 56 that is configured to drive rotation of the single-piece structure 56 and the imaging components in response to a drive force (e.g., from a pulley or belt coupled to a motor). The drive mechanism 82 is located on the surface 84 (e.g., outer surface facing away from the axis of rotation 54) of the outer perimeter 86 of the first annular structure 58. In certain embodiments, the surface 84 of the drive mechanism 82 may include teeth (e.g., drive teeth or gear teeth). In certain embodiments, the drive mechanism 82 is flat or smooth. In certain embodiments, the drive mechanism 82 may include grooves. The drive mechanism 82 is disposed within the integrated CT gantry structure 104 between the CT rotating base 50 and the CT stationary frame 92. In particular, the drive mechanism 82 is located within the width 106 of the integrated gantry structure 104 (see FIG. 8).

The CT integrated gantry structure 104 includes the pulley or belt 130 coupled to the motor 132 and disposed about the drive mechanism 82 that provides a drive force. The drive mechanism 82 drives rotation of the single-piece structure 56 and the imaging components in response to a drive force (e.g., from the pulley or belt 130 coupled to the motor 132). As depicted, in certain embodiments with a larger drum diameter, the CT integrated gantry structure 104 includes a plain idler 134 coupled to the annular structure 96 of the CT stationary frame 92.

Figure 16:
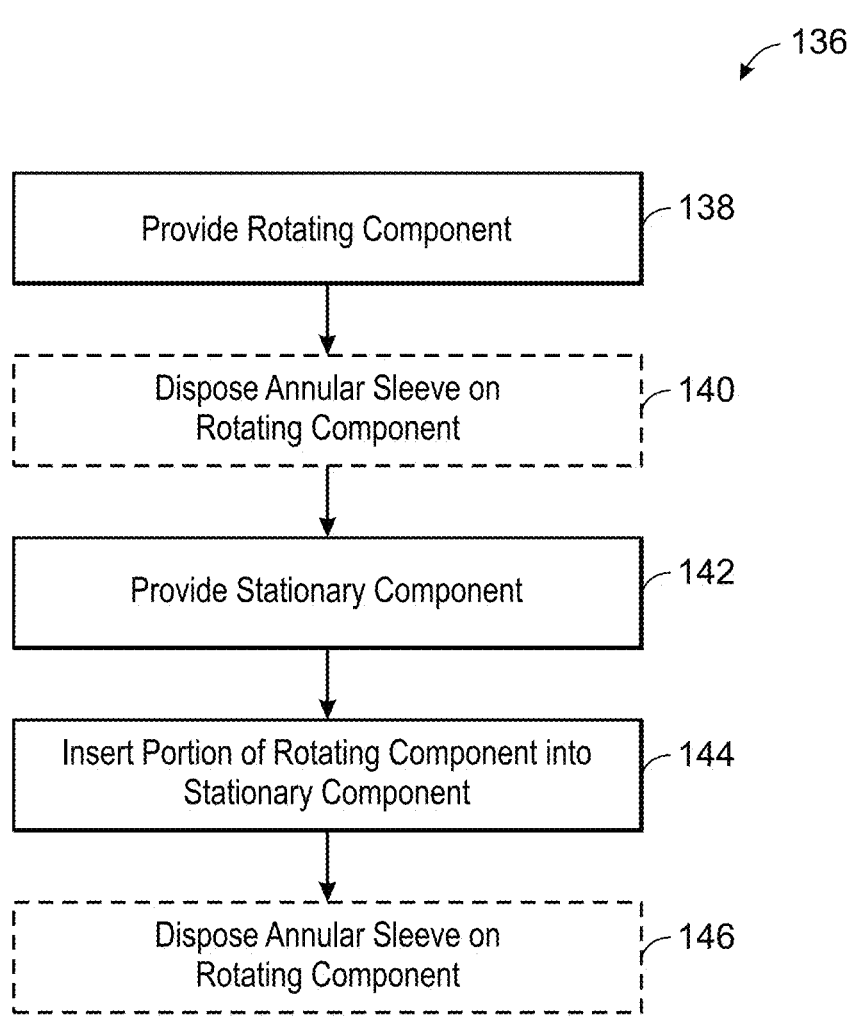
FIG. 16 is a method for forming (e.g., assembling) an integrated gantry structure of a computed tomography imaging system, in accordance with aspects of the present disclosure.

FIG. 16 is a method 136 for forming (e.g., assembling) an integrated gantry structure of a computed tomography imaging system. The method 136 includes providing a rotating component (e.g., CT rotating base) configured to couple to imaging components (block 138). The rotating component includes a drive mechanism integrated on the rotating component configured to drive rotation of the rotating component and the imaging components in response to a driving force. In certain embodiments, the method 136 also includes disposing an annular retainer sleeve about the rotating component (e.g., when the annular sleeve is configured to abut a front side of an annular structure of the CT stationary frame) (block 140). The method 136 further includes providing a stationary component (e.g., stationary frame) configured to support the rotating component (block 142). The method 136 even further includes inserting a portion of the rotating component into the stationary component with a bearing disposed within an annular recess defined by the portion of the rotating component and the stationary component (block 144). In certain embodiments (e.g., when the annular sleeve is configured to be disposed on a front side of annular structure of the CT stationary frame), the portion of the rotating component is inserted until the annular retainer sleeve abuts the stationary component adjacent the annular recess to keep the rotating component coupled to the stationary component via the bearing. In certain embodiments, the method 136 includes disposing the annular retainer sleeve about the rotating component so that the retainer sleeve abuts a rear side of the annular structure of the stationary component adjacent the annular recess to keep the rotating component coupled to the stationary component via the bearing (block 146).

Technical effects of the disclosed embodiments include providing an integrated stationary and rotating structure (e.g., rotating base or drum) for a CT gantry with a unified drive having multiple features such as an integrated bearing, an integrated drive mechanism, and mounting interfaces for various imaging components of the CT imaging system (e.g., X-ray source (e.g., X-ray tube), collimator, and X-ray detector assembly). Technical effects of the disclosed embodiments also include providing a rotating drum that is integrated directly (i.e., directly coupled) with the CT stationary frame via a wire race bearing, thus, eliminating the need for a separate externally mounted bearing. Unlike existing gantry structures having a rotating component with an endoskeleton structural architecture (i.e., rotating components are fitted inside the CT rotating base skeleton), the disclosed embodiments utilize an exoskeleton structural architecture (i.e., rotating components are projecting outside the CT rotating base skeleton) which results in a more compact footprint for the overall CT system. The unified drive solution of the rotating drum makes the entire gantry structure plug and play fit, thus, eliminating any misalignments with the drive-driven system and enhancing motion performance. The integration of all of the components into a single integrated component eliminates the assembly alignment process of a drive wheel with respect to the rotating drum, eliminates the assembly alignment process of a rotating drum to a separate external bearing, and eliminates the assembly alignment process of a separate external bearing to a CT stationary frame.

Technical effects of the disclosed embodiments further include providing improved image quality due to reduced gantry motion due to the integrated parts and elimination of tolerance stack up (e.g., due to fewer rotor deformations and better control of deformations in image chain components). Also, the elimination of tolerance stack up (due the integrated gantry structure) helps in alignment of X-ray tube and X-ray detector assembly and, thus, eliminates beam on window alignment requirement. Technical effects of the disclosed embodiments also include providing more structural robustness and rigidity, thus, making it scalable to higher rotation speed to help in providing a faster scan time and a reduced X-ray dose provided to the patient.

Technical effects of the disclosed embodiments include eliminating the use of Class-A bolted joints which results in a more robust and safer product. Technical effects of the disclosed embodiments also include eliminating the run out alignment of a driven pulley with respect to a center of rotation, thus, reducing time and effort during assembly. The disclosed embodiments also do not require any special handling during both manufacturing and assembly since the rotating drum, bearing, stationary frame, and pulley are integrated into a single component. Technical effects of the disclosed embodiments further include reducing assembly time and providing a lower part count (resulting in less inventory at manufacturing). Technical effects of the disclosed embodiments also include reducing labor cost during manufacturing due to the simplification of the assembly process and reduction in parts to assemble. Technical effects of the disclosed embodiments include also providing an integrated gantry structure having a lower carbon footprint and a compact form configured to fit into the least amount of space for installation due to a lesser Z-depth.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An integrated gantry structure of a computed tomography (CT) imaging system, comprising:
   a rotating component configured to couple to imaging components, wherein the rotating component comprises a drive mechanism integrated on the rotating component that is configured to drive rotation of the rotating component and the imaging components in response to a driving force, wherein the drive mechanism includes drive teeth;
   a stationary component configured to support the rotating component;
   a bearing disposed between the rotating component and the stationary component, wherein the bearing couples the rotating component to the stationary component, wherein the rotating component and the stationary component form an annular recess, and the bearing is disposed within the annular recess; and wherein the rotating component comprises a first annular structure having an outer surface facing away from a rotational axis of the rotating component in a radial direction perpendicular to the rotational axis, and the stationary component comprises a second annular structure having an inner surface facing toward the rotational axis in the radial direction, and wherein the annular recess is formed between an interface between the outer surface and the inner surface; and
   an annular retainer sleeve disposed about the outer surface of the first annular structure while abutting a lateral surface of the second annular structure, wherein the annular retainer sleeve is configured to keep the rotating component coupled to the stationary component via the bearing.

2. The integrated gantry structure of claim 1, wherein the rotating component comprises a single-piece structure.

3. The integrated gantry structure of claim 2, wherein the imaging components comprise an X-ray source, a collimator, and an X-ray detector assembly.

4. The integrated gantry structure of claim 1, further comprising a pulley or belt coupled to a motor disposed between the rotating component and the stationary component, wherein the pulley or belt coupled to the motor is configured to provide the driving force.

5. The integrated gantry structure of claim 1, wherein the drive mechanism is located on the outer surface of the first annular structure adjacent a portion of the outer surface that interfaces with the inner surface of the second annular structure that forms the annular recess.

6. The integrated gantry structure of claim 5, wherein the annular retainer sleeve is disposed about the outer surface of the first annular structure between the drive mechanism and the portion of the outer surface that interfaces with the inner surface of the second annular structure that forms the annular recess.

7. The integrated gantry structure of claim 5, wherein the portion of the outer surface that interfaces with the inner surface of the second annular structure that forms the annular recess is disposed between the drive mechanism and where the annular retainer sleeve is disposed about the outer surface of the first annular structure.

8. The integrated gantry structure of claim 1, wherein the bearing comprises a wire race bearing.

9. The integrated gantry structure of claim 8, wherein the wire race bearing comprises races made of an elastomer configured to dampen noise during rotation of the rotating component, to keep a bearing preload within a desired range, and to form an electrical insulation between the rotating component and the stationary component.

10. A computed tomography (CT) imaging system, comprising:
   an integrated gantry structure, comprising:
      a rotating component configured to couple to imaging components, wherein the rotating component comprises a drive mechanism integrated on the rotating component that is configured to drive rotation of the rotating component and the imaging components in response to a driving force, wherein the drive mechanism includes drive teeth;
      a stationary component configured to support the rotating component, wherein the rotating component and the stationary component form an annular recess, wherein the rotating component comprises a first annular structure having an outer surface facing away from a rotational axis of the rotating component in a radial direction perpendicular to the rotational axis, and the stationary component comprises a second annular structure having an inner surface facing toward the rotational axis in the radial direction, and wherein the annular recess is formed between an interface between the outer surface and the inner surface;

a wire race bearing disposed within the annular recess; and an annular retainer sleeve disposed about the outer surface of the first annular structure while abutting a lateral surface of the second annular structure, wherein the annular retainer sleeve is configured to keep the rotating component coupled to the stationary component via the wire race bearing.

11. The CT imaging system of claim 10, further comprising a pulley or belt coupled to a motor disposed between the rotating component and the stationary component, wherein the pulley or belt coupled to the motor is configured to provide the driving force.

12. The CT imaging system of claim 10, wherein the drive mechanism is located on the outer surface of the first annular structure adjacent a portion of the outer surface that interfaces with the inner surface of the second annular structure that forms the annular recess.

13. The CT imaging system of claim 12, wherein the annular retainer sleeve is disposed about the outer surface of the first annular structure between the drive mechanism and the portion of the outer surface that interfaces with the inner surface of the second annular structure that forms the annular recess.

14. A method for forming an integrated gantry structure of a computed tomography imaging system, comprising:

providing a rotating component configured to couple to imaging components, wherein the rotating component comprises a drive mechanism integrated on the rotating component that is configured to drive rotation of the rotating component and the imaging components in response to a driving force, wherein the drive mechanism includes drive teeth;

disposing an annular retainer sleeve about the rotating component;

providing a stationary component configured to support the rotating component;

inserting a portion of the rotating component into the stationary component with a bearing disposed within an annular recess defined by the portion of the rotating component and the stationary component, wherein the portion of the rotating component is inserted until the annular retainer sleeve abuts the stationary component adjacent the annular recess to keep the rotating component coupled to the stationary component via the bearing.

* * * * *